(12) United States Patent
Grech et al.

(10) Patent No.: US 7,708,799 B2
(45) Date of Patent: May 4, 2010

(54) DITHIOCARBAMATES AND PHOSPHITE FORMULATIONS

(75) Inventors: Nigel Grech, Reedley, CA (US); John L. Peterson, Visalia, CA (US)

(73) Assignee: Plant Protectants, LLC, Visalia, CA (US)

( * ) Notice: Subject to any disclaimer, the term of this patent is extended or adjusted under 35 U.S.C. 154(b) by 0 days.

(21) Appl. No.: 11/440,164

(22) Filed: May 23, 2006

(65) Prior Publication Data

US 2006/0283223 A1    Dec. 21, 2006

Related U.S. Application Data

(60) Provisional application No. 60/683,812, filed on May 23, 2005.

(51) Int. Cl.
 *C05D 9/00* (2006.01)
(52) U.S. Cl. .................. 71/29; 27/28; 27/32; 27/64.1; 27/64.06
(58) Field of Classification Search ............ 71/32, 71/64.08, 64.1, 27, 64.06, 28, 29
See application file for complete search history.

(56) References Cited

U.S. PATENT DOCUMENTS

| | | | |
|---|---|---|---|
| 1,976,905 A | 10/1934 | Thordarson | |
| 2,663,628 A | 12/1953 | Thomsen | |
| 3,342,598 A | 9/1967 | Bard | |
| 3,798,020 A | 3/1974 | Parham et al. | |
| 3,941,896 A | 3/1976 | Smith et al. | |
| 3,969,293 A | 7/1976 | White et al. | |
| 4,058,600 A * | 11/1977 | Debourge et al. | 424/601 |
| 4,066,390 A | 1/1978 | Christie et al. | |
| 4,075,324 A * | 2/1978 | Thizy et al. | 424/601 |
| 4,119,724 A | 10/1978 | Thizy et al. | |
| 4,125,393 A | 11/1978 | Kohl et al. | |
| 4,139,616 A | 2/1979 | Ducret et al. | |
| 4,334,905 A | 6/1982 | Wagner et al. | |
| 4,482,372 A | 11/1984 | Palgrave et al. | |
| 4,542,023 A | 9/1985 | Lacroix et al. | |
| 4,581,056 A | 4/1986 | Nooden et al. | |
| 4,698,334 A | 10/1987 | Horriere et al. | |
| 4,755,614 A | 7/1988 | Corbet et al. | |
| 4,780,458 A | 10/1988 | Hodakowski et al. | |
| 4,806,445 A | 2/1989 | Horriere et al. | |
| 4,849,219 A * | 7/1989 | Staub et al. | 424/605 |
| 4,935,410 A | 6/1990 | Barlet | |
| 5,070,083 A | 12/1991 | Barlet | |
| 5,099,049 A | 3/1992 | Chamberlain | |
| 5,124,344 A | 6/1992 | Greiner et al. | |
| 5,133,891 A | 7/1992 | Barr et al. | |
| 5,169,646 A | 12/1992 | Horriere et al. | |
| 5,174,806 A | 12/1992 | Masuda | |
| 5,206,228 A | 4/1993 | Collins | |
| 5,246,953 A | 9/1993 | Greiner et al. | |
| 5,336,661 A | 8/1994 | Lucas | |
| 5,395,418 A | 3/1995 | Vetanovetz et al. | |
| 5,514,200 A | 5/1996 | Lovatt | |
| 5,573,164 A | 11/1996 | Law | |
| 5,616,532 A | 4/1997 | Heller et al. | |
| 5,656,281 A | 8/1997 | Hytte et al. | |
| 5,665,672 A * | 9/1997 | Lucas | 504/126 |
| 5,667,795 A | 9/1997 | Fraley et al. | |
| 5,707,418 A | 1/1998 | Hsu | |
| 5,736,164 A | 4/1998 | Taylor | |
| 5,736,313 A | 4/1998 | Spargo et al. | |
| 5,800,837 A | 9/1998 | Taylor | |
| 5,830,255 A | 11/1998 | Lovatt | |
| 5,865,870 A | 2/1999 | Hsu | |
| 5,939,357 A | 8/1999 | Jones et al. | |
| 6,113,655 A | 9/2000 | Lovatt | |
| 6,168,643 B1 | 1/2001 | Hsu | |
| 6,169,057 B1 | 1/2001 | Lovatt | |
| 6,387,145 B1 | 5/2002 | Miele et al. | |
| 2004/0035162 A1 | 2/2004 | Williams et al. | |
| 2004/0241250 A1 | 12/2004 | Rajamannan | |
| 2006/0084573 A1 * | 4/2006 | Grech et al. | 504/101 |

FOREIGN PATENT DOCUMENTS

| | | | |
|---|---|---|---|
| DE | 3417133 | | 7/1985 |
| FR | 2359077 | | 7/1976 |
| FR | 2389587 | | 1/1979 |
| GB | 2095114 A | * | 9/1982 |
| GB | 2238960 A | * | 6/1991 |
| JP | 61-291482 | | 12/1986 |
| JP | 4-74784 | | 3/1992 |
| NZ | 247805 | | 6/1993 |
| NZ | 248351 | | 8/1993 |

(Continued)

OTHER PUBLICATIONS

*Rhone-Poulenc Agrochime , S.A.* v. *Biagro Western Sales Inc.*, 1994 U.S. Dist. LEXIS 20754; 35 U.S. P.Q.2D (BNA) 1203; no month.

(Continued)

*Primary Examiner*—C. Sayala
(74) *Attorney, Agent, or Firm*—Morgan, Lewis and Bockius, LLP

(57) ABSTRACT

Dithiocarbamate and phosphite containing fertilizers, as well as methods of making and methods of using these fertilizers, are disclosed.

12 Claims, 4 Drawing Sheets

FOREIGN PATENT DOCUMENTS

| NZ | 280498 | 11/1995 |
|---|---|---|
| NZ | 227167 | 12/1998 |
| NZ | 511086 | 10/1999 |
| RU | 655373 | 4/1979 |
| WO | WO 86/00613 | 1/1986 |
| WO | WO 2002/014238 | 2/2002 |

OTHER PUBLICATIONS

*Biagro Western Sales, Inc.* v. *Helena Chemical Company*, 160 F. Supp 2d 1112; 2001 U.S. Dist. LEXIS 21698, no month.
*Biagro Western Sales, Inc.* v. *Helena Chemical Company*, 160 F. Supp 2d 1136; 2001 U.S. Dist. LEXIS 21704, no month.
*Biagro Western Sales, Inc. and The Regents of the University of California* v. *Grow More, In.*, filed Aug. 15, 2002 [Order (1) Denying Plaintiffs' motion for Reconsideration and (2) Directing the Parties to Submit Further Briefing on the Issue of Prosecution History Estoppel].
*Biagro Western Sales, Inc.* v. *Grow More, Inc.*, filed Apr. 9, 2003 [Order Denying Plaintiffs' Motion for Reconsideration].
*The Regents of the University of California and Biagro Western Sales, Inc.* v. *Actagro, LLC*, 2004 U.S. App. LEXIS 15663, no month.
*Biagro Western Sales, Inc. and The Regents of the University of California* v. *Grow More, Inc.*, 423 F.3d 1296, CA Fed. (Cal.), 2005; 76 U.S.P.Q. 2d 1347, no month.
Adams, et al. "Transition of Phosphite to Phosphate in Soils" *Soil Science* (1953) vol. 75, pp. 361-371.
Agrichem Product Information Brochure for "Supa Stand Phos: Supa Crop," subtitled "For the Cotton and Corn Farmer," published by Agrichem Manufacturing Ind.: Australia, 1 page (Oct. 1990).
Agrichem Product Information Brochure for "Supa Stand Phos: Supa Protective Pop-Up Starter," published by Agrichem Manufacturing Ind.: Australia, 2 pages (Aug. 1990).
Agrichem Manufacturing Ind., "Water Injection and Foliar Trials 1990/91: Cotton & Maize" published by Agrichem Manufacturing Ind.: Australia (1990-1991), 3 pages.
Aly, et al. "Effect of Meteorological Factors and Fertilization on Barley Powdery Mildew Infection" *Agricultural Research Review* (1987) vol. 65(2), pp. 233-242.
Bedi, et al. "Influence of Nitrogen, Phosphorus and Potassium on the Development of Early Blight of Tomato" *Indian Phytopathology* (1983) vol. 36(3), pp. 546-548.
Product catalog of Biagro (Bioestimulantes Agricolas, S.A.), a Spanish company, undated but believed to be before Feb. 7, 1993, (with one English translation of the entire fifth page (the page containing Metalosate-F product) and another English translation of only the three Metalosate product on the fifth page).
Bompeix e al., "Modalités de l'obtention des nécroses bloquantes sur feuilles détachées de Tomate par l'action du tris-O-éthyl phosphonate d'aluminium (phoséthyl d'aluminium), hypothéses sur son mode d'action in vivo," Ann. Phytophathol., 12:4, pp. 337-351, 1980 (French with English translation)., no month.
Bompeix et al., "Mode d'action du phoseéthyl al," Phytiatrie-Phytopharmacie, 30, pp. 257-272, 1981 (French with English translation), no month.
Brennan, et al "Effect of Superphosphate and Superphosphate Plus Flutriafol on Yield and Take-all of Wheat" *Australian Journal of Experimental Agriculture* (1989) vol. 29(2), pp. 247-252.
Letter from the California Department of Food and Agriculture, dated Nov. 17, 1993, to Biagro Western Sales, Inc., and attached labeling information.
California Fertilizer Association, "Western Fertilizer Handbook" *Soil Improvement Committee, California Fertilizer Association, Horticulture Ed. Interstate Publishers, Danville, Ill.* (1990).
Clark, et al. "Fertilizer Trial Using Water Injection Technique with Supracrop Products" *Report by D.Q. Clark & Associates Pty Ltd.* (Jul. 1991), 8 pages.
Coffey, et al. "Phosphonates: Antifungal Compounds Against Oomycetes" *California Avocado Growers Yrbk Nitrogen, Phosphorus and Sulphur Utilization by Fungi Symposium of the British Mycological Society* (1988), pp. 106-129.

Cook, A.A., "Genetics of Resistance in Capsicum Annuum to Two Virus Diseases" *Phytopathology* (May 1960) vol. 50, pp. 364-365.
Dabash, et al. "Relation Between Fertilizers and White Rot Disease of Onion with Reference to the Rhizosphere" *Agricultural Research Review* (1985) vol. 63(2), pp. 99-110., no month.
Embleton, et al. "Leaf Analysis Standards" *The Citrus Industry: Proc. Int. Soc. Citriculture* (1978) pp. 184-186.
Engelhard, Arthur W. "Historical Highlights and Prospects for the Future" *Soilborne Plant Pathogens: Management of Diseases with Macro- and Microelements APS Press: The American Phytopathological Society, St. Paul, Minnesota* ( 1989) pp. 9-15.
Engelhard, Arthur W. (editor) "Definition of Phosphorus and Potassium" *Soilborne Plant Pathogens: Management of Diseases with Macro- and Microelements): APS Press: The American Phytopathological Society, St. Paul, Minnesota*, pp. 55-56.
Fahmy, et al. "Some Factors Affecting the Incidence of Potato Brown Rot" *Assiut Journal of Agricultural Sciences* (1990) vol. 21(5), pp. 221-230.
Fenn, et al. "Studies on the In Vitro and In Vivo Antifungal Activity of Fosetyl-Al and Phosphorous Acid" *Phytopathology* (1983), vol. 74, pp. 606-611.
Fenn, et al. "Quantification of Phosphonate and Ethyl Phosphonate in Tobacco and Tomato Tissues and Significance for the Mode of Action of Two Phosphonate Fungicides" *Phytopathology* (1989) vol. 79(1), pp. 76-82.
Fraizer, et al. "Crystallography and Equilibrium Solubility for Ammonium and Potassium Orthophosphites and Hypophosphites" *Fertilizer Research* (1992) vol. 32, pp. 161-168.
Gottstein, et al. "Induction of Systemic Resistance to Anthracnose in Cucumber by Phosphates" *Phytopathology* (Aug. 1989) vol. 79, pp. 176-179.
Graham, et al. "Phytophthora Root Rot Development on Mycorrhizal and Phosphorus-fertilized Nonmycorrhizal Sweet Orange Seedlings" *Plant Disease* (1988) vol. 72(7), pp. 611-614.
Granade, et al. "Increasing Yield and Reducing Disease on Wheat with P and K Fertilization" *Better Crops with Plant Food* vol. 74(2), pp. 26-27, 30.
Griffith, et al. "Crop Responses at High Soil Test Phosphorus Levels" *Better Crops with Plant Food Published by the Potash & Phosphate Institute (PPI) Norcross, Georgia* (Fall 1992), 2 pages.
Grossl, et al. "Precipitation of Dicalcium Phosphate Dihydrate in the Presence of Organic Acids" *Soil Science Society of America Jour.* (May-Jun. 1991) col. 55(3), p. 670-675.
Guest and Grant, "The Complex Action of Phosphonates as Antifungal Agents," *Biological Review* (1991) vol. 66, pp. 159-187.
Gupta, et al. "Effect of Fertilizer Application on Severity of Sooty Stripe of Sorghum (Sorghum Bicolor) Caused by *Ramulispora sorghi*" *Indian Journal of Agricultural Sciences* (1990) vol. 60 (1), pp. 76-77.
Hartley et al., part of "Experimental Methods for Studying Equilibria I," chapter 7 in Solution Equilibia, Ellis Norwood Limited, 1980, pp. 124-127., no month.
Huber, Dr. Don M., "Micronutrients and Plant Disease" *Crop Management, Ag Consultant* (Feb. 1994).
Huber, Dr. Don M., "Introduction for: Soilborne Plant Pathogens: Management of Diseases with Macro- and Microelements" Engelhard, Arthur W. (editor): *APS Press: The American Phytopathological Society, St. Paul, Minnesota* (1989) pp. 1-8.
Jaffe, B.A., "Influence of Root Biomass on Number of *Pratylenchus penetrans* Within Host Roots" *Phytopathology* (Jun. 1980) vol. 70, pp. 1214-1216.
Jayaraj, et al. "Effect of Potash Nutrition on the Stem Rot Incidence and Yields of Rice" *Journal of Potassium Research* (1991) vol. 7(1), pp. 62-66.
Jeyraman, et al. "Role of Potassium Treatment on Yield and Incidence of Pests and Disease in Chilli" *Journal of Potassium Research* (1988) vol. 4(2), pp. 67-70.
Karwasra, et al. "Host Nutrition in Relation to Soft Rot Incidence in Potato" *Plant Disease Research* (1990) vol. 5(2), pp. 170-174.
Lovatt, Carol J., "A Definitive Test to Determine Whether Phosphite Fertilization Can Replace Phosphate Fertilization to Supply P in the Metabolism of 'Hass' on 'Duke 7.' A Preliminary Report," California Avocado Society 1990 Yearbook, 74, pp. 61-64 (1990)., no month.

Lovatt, Carol J., "A Definitive Test to determine Whether Phosphite Fertilization Can Replace Phosphate Fertilization to Supply P in the Metabolism of 'Hass' on 'Duke 7.' A Preliminary Report," 4 pages (1992)., no month.

Lovatt, "Avocado Research Project Plan and Grant Requirements," a grant proposal presented to the California Avocado Society for fiscal year 1990-1991., no month.

Lovatt, Carol J. "A Definitive Test to Determine Whether Phosphite Fertilization can Replace Phosphate Fertilization to Supply P in the Metabolism of 'Hass' on Duke 7.—a Preliminary Report" *Proc. of Second World Avocado Congress* (1992), *Unknown Citrograph* (1990) vol. 75(7), p. 161.

Lovatt, Carol J., "Foliar Phosphorous Fertilization of Citrus by Foliar Application of Phosphite" *Summary of Citrus Research* (1990), pp. 25-26.

Lucas et al., "Phosphite Injury to Corn," Agronomy Journal, 71, pp. 1063-1065, 1979., no month.

Mac Intire, et al. "Fertilizer Evaluation of Certain Phosphorus, and Phosphoric Materials by Means of Pot Cultures" *Agronomy Journal* (Nov. 1950), vol. 42(11), p. 543-549.
Mahadevamurthy, et al. "Effect of Fertilizer Amendment of Soil and Antagonist Treatment on Sclerotial Germination on *Claviceps Fusiformis" Plant Disease Research* (1990) vol. 5(2), pp. 212-215.
Malacinski and Konetzka, "Bacterial Oxidation of Orthophosphite," Journal of Bacteriology, vol. 91, 578-582, (1966).
Mattingly, et al. "Progress in the Chemistry of Fertilizer and Soil Phosphorus" *Topics in Phosphorus Chemistry* (1967) vol. 4, pp. 157-290.
Mc Lean, Ben, "The Effects of Nitrogen, Phosphorous, and Potassium Fertilization on Citrus Fruit Quality" (Apr. 1991) found in *Reports for HOS 6412 Nutrition of Horticulture Crops Vegetable Crops Department Institute of Food and Agriculture Sciences, University of Florida: Review Papers* (Spring 1991) by Locascio, Dr. S. J.
Miyake, et aL "Phosphate Response of Rice in Indonesian Paddy Fields" *Technical Bulletin of the Tropical Agriculture Research Center* (1984) No. 17, pp. 1-78.
Mohit-Singh, et al. "Effect of Interaction of Nitrogen, Phosphorus and Potash on Alternaria Leaf Sport and Fruit Rot of Brinjal" *Farm Science Journal* (1988) vol. 3(1), pp. 21-23. CAB Abstract.
Mucharromah, et al. "Oxalate and Phosphates Induce Systemic Resistance Against Diseases Caused by Fungi, Bacteria and Viruses in Cucumber" *Kentucky Agricultural Experiment Station journal paper* (Jul. 1990), 6 pages.
Muchovej et al., "Effect of Exchangeable Soil Aluminum and Alkaline Calcium Salts on the Pathogenicity and Growth of *Phytophthora capsici* from Green Pepper," Phytopathology, 70, pp. 1212-1214, 1980., no month.
Mustika, et al. "Control of Pepper Yellow Disease with Fertilizer and Pesticides" *Pemberitaan, Penelitian Tanaman Industri Indonesia* (1984) vol. 9(50), pp. 37-43.
Nayudu, et al. "Bacterial Spot of Tomato as Influenced by Temperature and by Age and Nutrition of the Host" *Phytopathology* (May 1960) vol. 50, pp. 360-363.
Neilsen, et al. "Repsonse of Fruit Trees to Phosphorus Fertilization" *Acta Horticulturae* (1990) No. 274, pp. 347-359.
Obreza, et al. "Citrus Fertilizer Management on Calcareous Soils" *Circular 1127, a series of the Soil and Water Science Department; Florida Cooperative Extension Service* (Dec. 1993), pp. 1-9.
Ouimette, et al. "Comparative Antifungal Activity of Four Phosphonate Compounds Against Isolates of Nine *Phytophthora* Species" *Phytopathology* (Feb. 1989) vol. 79(7), pp. 761-767.
Prusky and Keen, "Involvement of Preformed Antifungal Compounds in the Resistance of Su87btropical Fruits to Fungal Decay" *Plant Disease* (1993) vol. 77(2), pp. 114-119.
Rashid, et al. "Effects of Nitrogen, Phosphorus and Sulfur Fertilizer Combinations on the Severity of *Alternaria, Drechslera* and Bacterial Leaf Blights of Wheat" *Bangladesh Journal of Plant Pathology* (1985) vol. 1(1) pp. 33-39. CAB Abstract, no month.
Reis, et al. "Effect of Mineral Nutrition on Take-all of Wheat" *Ecology and Epidemiology: Phytopathology* (1982) vol. 72(2), pp. 224-229., no month.
Robertson and Boyer, "The Biological Inactivity of Glucose 6-Phosphite, Inorganic Phosphites and Other Phosphites," Archives of Biochemistry and Biophysics, vol. 62, 380-395, 1956., no month.
Robertson, et al. "Orthophosphite as a Buffer for Biological Studies" *Archives of Biochemistry and Biophysics* (1956), vol. 62, pp. 396-401., no month.
Rothbaum et al., "The Use of Red Phosphorus as a Fertiliser. Part 1. Rates of Oxidation of Red Phosphorus in Soil," New Zealand Journal of Science, 7, pp. 51-66, 1964., no month.
Rothbaum and Kitt, "The Use of Red Phosphorus as a Fertiliser. Part 2. Extended Studies on Oxidation Rates of Red Phosphorus," New Zealand Journal of Science, 7, pp. 67-74, 1964., no month.
Rothbaum and Baillie, "The Use of Red Phosphorus as a Fertiliser. Part 4. Phosphite and Phosphate Retention in Soils," New Zealand Journal of Science, 7, pp. 446-451, 1964., no month.
Rothbaum, H.P., "The Use of Red Phosphorus as a Fertiliser. Part 5. The Effect of Copper on the Oxidation Reaction of Red Phosphorus," New Zealand Journal of Science, 8, pp. 388-397, 1965., no month.
Simpson, Ken "Fertilizers and Manures" Published by Harlow, Essex, England: Longman Scientific & Technical; New York: J. Wiley & Sons (1991).
Smilke, et al. "The Mode of Action of Phosphite: Evidence for Both Direct and Indirect Modes of Action on Three *Phytophthora* spp. in Plants" *Phytopathology* (1989) vol. 79(9), pp. 921-926.
Sparks, "Growth of Nutrition of Pecan Seedlings from Potassium Phosphate Foliar Sprays" Hort-Science, (1986) vol. 21, pp. 451-453.
Sugar, et al. "Management of Nitrogen and Calcium in Pear Trees for Enhancement of Fruit Resistance to Postharvest Decay" *Hort Technology* (Jul.-Sep. 1992) vol. 2(3), pp. 382-387.
Sukarno et al., "The Effect of Fungicides on Vesicular-Arbuscular Mycorrhizal Symbiosis," *New Phytologist* (1993)vVol. (25), pp. 139-147.
Thompson, et al. "Liming and Southern Crops: A Working Partnership" *Better Crops with Plant Food: Published by the Potash & Phosphate Institute (PPI) Norcross, Georgia* (1993/1994), pp. 18-19.
Toerlen and Slabbert, "Phosphorous Nutrition of Avocados Through Truck Injection," Avocado Grower, p. 10, Jan. 1985.
Tsubota, Goro, "Phosphate Reduction the Paddy Field I, Soil and Plant Food," (1959) vol. 5(1), pp. 10-15.
Unknown, "Foliar Applications Do Double Duty" *Citograph* (May 1990) vol. 75(7), p. 161.
Unknown, Abstract entitled "Agricola (1970-1978)," (unknown publication), 1 page, 1992.
Labels for "Resistim," a product of Mandops (UK) Limited, undated but believed to be before Feb. 7, 1993.
Unknown, "Don't Back Away from a Phosphite Confrontation," (unknown publication), p. 5, Apr. 21, 1992.
Walters, et al. "Induction of Systemic Resistance to rust in *Vicia faba* by Phosphate and EDTA: Effects of Calcium" *Plant Pathology* (1992) vol. 4, pp. 444-448.
Ward, B. W., "Assessing Phosphorus Buildup in Crop Acreage—The Upper Vermilion Watershed Project", *Better Crops with Plant Food: Published by the Potash & Phosphate Institute (PPI) Norcross, Georgia* (1993/1994), pp. 16-17.
Watt, H.V.H. van der, et al. "Amelioration of Subsoil Acidity by Application of a Coal-derived Calcium Fulvate to the Soil Surface" *Nature* (1991) vol. 350(6314), pp. 146-148.
W.B. McLean & Sons of Clermont Florida, *Correspondence to Mr. Bill Paul*; (Dec. 28, 1993), 2 pages.
W.B. McLean & Sons of Clermont Florida, *Correspondence to Mr. Bill Paul*; (Feb. 4, 1994), 2 pages.
Widdowson (and Rothbaum) et al., "The Use of Red Phosphorus as a Fertiliser. Part 3. Spot Trials with Perennial Ryegrass and White Clover," New Zealand Journal of Science, 7, pp. 427-455, 1964., no. month.
Windhols, M. (editor) "Definition of Calcium Phosphate ($CAHPO_3$)" *Merck Index, 11th ed.* (1994) p. 256.
Yuda et al, "Search for Efficient Phosphorus Fertilization," Proc. Intern'l. Soc. Citriculture, 1981., no month.

* cited by examiner

Mancozeb x is a number between 1 and about 1,000,000;
y is a number between 1 and about 1,000,000;
The ratio of x to y is about 10:1

Maneb n is a number between 1 and about 1,000,000

Metiram x is a number between 1 and about 1,000,000;
y is a number between 1 and about 1,000,000;
The ratio of x to y is about 3:1

Thiram (or Thiuram)

Zineb n is a number between 1 and about 1,000,000

FIG. 3A
FIG. 3B
 
Calciphite + Mancozeb
(Mancozeb at 50 ppm)
Mancozeb
(Mancozeb at 100 ppm)
Spore Germination Inhibition

DITHIOCARBAMATES AND PHOSPHITE FORMULATIONS

CROSS-REFERENCES TO RELATED APPLICATIONS

The present application claims priority to U.S. Provisional Patent Application No. 60/683,812, filed May 23, 2005; which is incorporated herein by reference in its entirety for all purposes.

BACKGROUND OF THE INVENTION

In the past, compositions of dithiocarbamate and phosphorous have been utilized as fungicides. For example, U.S. Pat. No. 4,698,334 to Horriere et al. and U.S. Pat. No. 4,806,445 to Horriere et al. propose fungicidal compositions based on alkyl phosphites in combination with various contact fungicides such as mancozeb. U.S. Pat. No. 4,139,616 to Ducret et al. describes fungicidal compositions based on alkyl phosphites. U.S. Pat. No. 5,336,661 to Lucas et al. and U.S. Pat. No. 5,665,672 to Lucas et al. describe fungicidal compositions based on monoester salts of phosphorous acid or alkyl phosphites and dithiocarbamates. None of these references describe compositions containing phosphite without alkyl substituents. Furthermore, none of these references describe the use of these compositions as fertilizers.

Water-dispersible granules of phosphite fungicial products have been described in the art. For example, U.S. Pat. No. 5,656,281 to Hytte et al. discloses concentrated fungicidal compositions with phosphite, dithiocarbamates and wetting agents or dispersing agents. All of the compositions in Hytte contain wetting agents or dispersing agents. Furthermore, Hytte does not describe the use of these compositions as fertilizers.

Phosphate has been known for its fertilizer properties since at least the 1990s through Lovatt (U.S. Pat. No. 5,514,200, which issued May 7, 1996; U.S. Pat. No. 5,830,255, which issued Nov. 3, 1998; U.S. Pat. No. 6,113,665, which issued Sep. 5, 2000; and U.S. Pat. No. 6,645,268 B2, which issued Nov. 11, 2003) (U.S. patent application Ser. No. 09/637,621, filed Aug. 11, 2000; Ser. No. 10/686,411, filed Oct. 14, 2003). Prior to this discovery, phosphite was relegated for use only as a fungicide (U.S. Pat. No. 4,075,324) and as a food preservative.

There still remains a need in the art for improved fertilizer and fungicide compositions that can efficiently provide phosphorous as well as other nutrients such as zinc and magnesium to a plant. These compositions should be easy to pour from a container and should be free of dispersants or wetting agents. The present invention fulfills this need, as well as others.

BRIEF SUMMARY OF THE INVENTION

The present invention discloses dithiocarbamate and phosphite containing fertilizers, as well as methods of making and methods of using these fertilizers.

Thus, in a first aspect, the invention provides a fertilizer concentrate comprising dithiocarbamate and at least one phosphite salt. The fertilizer concentrate is essentially devoid of dispersants and wetting agents.

In an exemplary embodiment, at least about 90% of the granules of said fertilizer concentrate have a diameter of from about 0.2 mm to about 4 mm. In an embodiment of the invention, the dithiocarbamate is a member selected from mancozeb, maneb, metiram, thiuram and zineb. In another embodiment of the invention, the phosphite salt is a member selected from monopotassium phosphite and dipotassium phosphite.

In an exemplary embodiment, the dithiocarbamate is present in an amount of from about 10% wt of dithiocarbamate/wt of fertilizer concentrate to about 35% wt of dithiocarbamate/wt of fertilizer concentrate. The phosphite salt is present in an amount of from about 15% wt of phosphite salt/wt of fertilizer concentrate to about 35% wt of phosphite salt/wt of fertilizer concentrate. The fertilizer concentrate also further comprises water in an amount of about 30% wt of water/wt of fertilizer concentrate to about 40% wt of water/wt of fertilizer concentrate.

In another aspect, the invention provides a fertilizer concentrate comprising a dithiocarbamate, which is present in an amount of from about 10% wt of dithiocarbamate/wt of fertilizer concentrate to about 35% wt of dithiocarbamate/wt of fertilizer concentrate; at least one phosphite salt, which is present in an amount of from about 15% wt of phosphite salt/wt of fertilizer concentrate to about 35% wt of phosphite salt/wt of fertilizer concentrate; a suspending agent, which is present in an amount of about 5% wt of suspending agent/wt of fertilizer concentrate; and water in an amount of about 30% wt of water/wt of fertilizer concentrate to about 40% wt of water/wt of fertilizer concentrate. In an exemplary embodiment, the dithiocarbamate is a member selected from mancozeb, maneb, zineb, thiram and metiram. In another exemplary embodiment, the phosphite salt is a member selected from monopotassium phosphite, dipotassium phosphite, calcium phosphite, monoammonium phosphite, diammonium phosphite, calcium hypophosphite and potassium hypophosphite. In yet another exemplary embodiment, the phosphite salt is calcium phosphite.

In a second aspect, the invention is a method of providing a fertilizer and a fungicide to a plant. This method comprises mixing water and a fertilizer of the invention, thus forming a use-dilution fertilizer. This use-dilution fertilizer is then applied to the foliage of a plant, thus providing the fertilizer and the fungicide to a plant.

In a third aspect, the invention provides a ready-to-use fertilizer, comprising a fertilizer concentrate of the invention and a diluent. In another embodiment of the invention, the diluent is a liquid. In another embodiment of the invention, the diluent is a solid. In another embodiment of the invention, the ratio of fertilizer concentrate to diluent is from about 1:10 to about 1:10,000. In another embodiment of the invention, the ratio of fertilizer concentrate to diluent is from about 1:20 to about 1:2,000.

Other objects and advantages of the invention will be apparent to those of skill in the art from the detailed description that follows.

BRIEF DESCRIPTION OF THE DRAWINGS

FIG. 3 displays the results, after 12 hours, of placing spores of the fungus *Mycosphearella* sp. on one agar plate (FIG. 3A) that contains calciphite and mancozeb, while the second agar plate (FIG. 3B) contains mancozeb and no calciphite. In the first agar plate, spore germination is greatly diminished, as compared with the second agar plate.

DETAILED DESCRIPTION OF THE INVENTION

I. A. Definitions

Figure 1A:
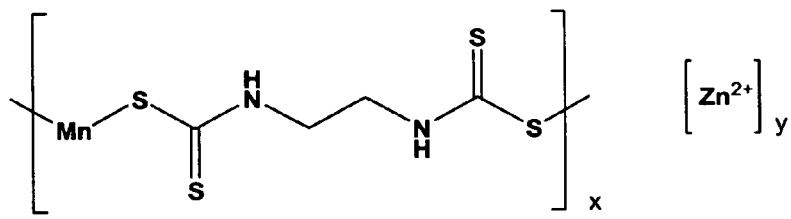
FIG. 1 is a table containing structures of exemplary dithiocarbamates of the invention. In this Figure, x is a number between 1 and about 1,000,000; y is a number between 1 and about 1,000,000; n is a number between 1 and about 1,000,000.
Figure 1A:
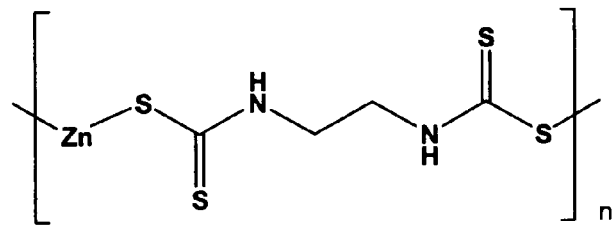
Figure 1A:
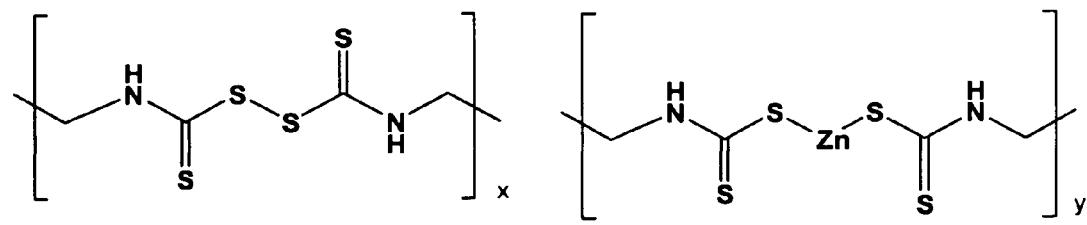
Figure 1B:
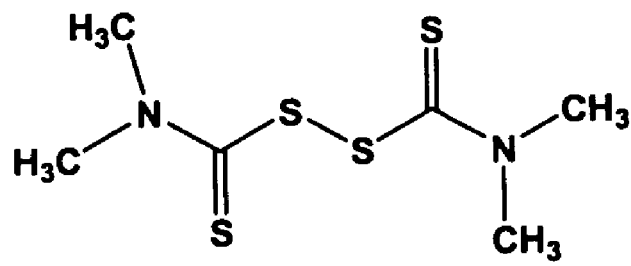
Figure 1B:
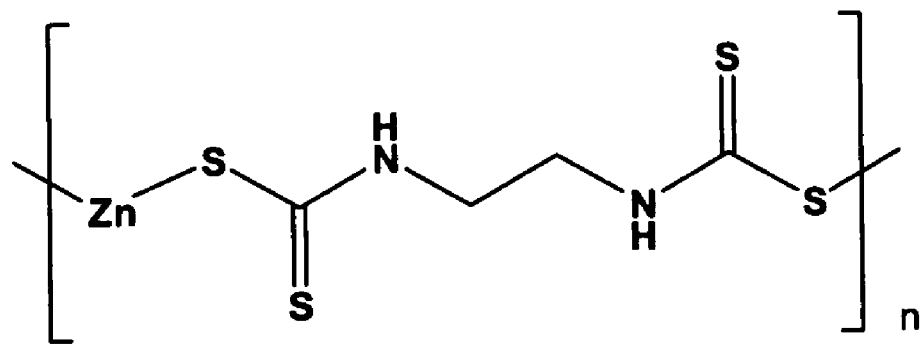

Unless defined otherwise, all technical and scientific terms used herein generally have the same meaning as commonly understood by one of ordinary skill in the art to which this invention belongs. Generally, the nomenclature used herein and the laboratory procedures in agriculture and chemistry are those well known and commonly employed in the art. Standard techniques are used synthesis of the compositions. The techniques and procedures are generally performed according to conventional methods in the art and various general references (see generally, Tisdale et al. SOIL FERTILITY AND FERTILIZERS, 6th ed. (1998) Prentice Hall, New York, which is incorporated herein by reference), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

The term "fertilizer", as used herein, means compositions which supply nutrients to, and stimulate the growth of, plants. A fertilizer can be a liquid or a solid.

The term "aqueous suspension", as used herein, means that the predominant liquid in the fertilizer is water. In some embodiments, the only liquid in the fertilizer is water. In other embodiments, there is more than one liquid in the fertilizer, but the predominant liquid is water. For example, the liquid portion of an aqueous suspension fertilizer can comprise 75% water and 25% soybean oil. An aqueous suspension can refer to either a liquid fertilizer concentrate or a liquid ready-to-use fertilizer.

The term "non-aqueous suspension", as used herein, means that the predominant liquid in the fertilizer is an oil. In some embodiments, the only liquid in the fertilizer is an oil. Examples of oils include soybean oil, canola oil, and mineral oil. In other embodiments, there is more than one liquid in the fertilizer, but the predominant liquid is oil. For example, the liquid portion of a non-aqueous suspension fertilizer can comprise 66% soybean oil and 33% water. A non-aqueous suspension can refer to either a liquid fertilizer concentrate or a liquid ready-to-use fertilizer.

The term "organic acid", as used herein, means a molecule that comprises carbon and that possess a pKa relative to water of about 10 or less.

The term "N—P—K", as used herein, means the amount of nitrogen, phosphorus, and potassium, in that order, that are present in a fertilizer in amounts equivalent to the weight percentages of N, $P_2O_5$, and $K_2O$. For example, a 10-20-15 fertilizer contains nutrients equivalent to 10% of N, 20% of $P_2O_5$, and 15% of $K_2O$ in weight/weight. Although the nutrients do not actually exist in a fertilizer in the forms of N, $P_2O_5$, or $K_2O$, these species are used as reference measures due to historic reasons.

The term "thickener", as used herein, means a material that increases the viscosity of a liquid. In this document, "thickener", "suspending agent", "stabilizing agent", "viscosity-increasing agent" and "binding agent" are used interchangeably.

The term "humectant", as used herein, means a compound that promotes retention and absorption of moisture.

The term "antimicrobial", as used herein, means capable of destroying or inhibiting the growth of microorganisms. In this document, "antimicrobial", "antibacterial" and "antibiotic" are used interchangeably.

The term "surfactant", as used herein, means a compound which reduces the surface tension of water. In this document, "surfactant", "detergent", "wetting agent" and "dispersant" are used interchangeably.

The term "plant growth regulator", as used herein, means a synthetic or naturally produced chemical that either inhibits or accelerates plant growth. In this document, "plant growth regulator" and "hormone" are used interchangeably.

The term "diluent", as used herein, means a material that is used to increase the size or volume of the fertilizer. A diluent can be either a liquid or a solid. Examples of liquid diluents include water, soybean oil, and mineral oil. Examples of solid diluents include clay, sand, peat and chalk.

The term "fertilizer concentrate", as used herein, means a fertilizer that requires the addition of a diluent prior to application to a plant. Fertilizer concentrates can be either liquid or solid. This term is sometimes known in the art as a "formulated product".

The term, "ready-to-use fertilizer", as used herein, means a material which, at a minimum, does not cause phytotoxicity after application to a plant. Under optimal conditions, this material will facilitate the uptake of calcium and phosphorus in a plant. This term is sometimes known in the art as a "tank mix".

The term, "fertilizers of the invention", as used herein, comprises fertilizer concentrates as well as ready-to-use fertilizers.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups, which are limited to hydrocarbon groups are termed "homoalkyl".

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$,—S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1 -piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") include both substituted and unsubstituted forms of the indicated radical. Preferred substituents for each type of radical are provided below.

Substituents for the alkyl, and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generally referred to as "alkyl substituents" and "heteroakyl substituents," respectively, and they can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, the aryl substituents and heteroaryl substituents are generally referred to as "aryl substituents" and "heteroaryl substituents," respectively and are varied and selected from, for example: halogen, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(N'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(Cl—C$_4$)alkyl, in a number ranging from zero to the total number of open valences on the aromatic ring system; and where R', R", R'" and R"" are preferably independently selected from hydrogen, (C$_1$-C$_8$)alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl. When a compound of the invention includes more than one R group, for example, each of the R groups is independently selected as are each R', R", R'" and R"" groups when more than one of these groups is present.

Two of the aryl substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-$(CH_2)_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —$(CRR')_s$—X—$(CR''R''')_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted ($C_1$-$C_6$)alkyl.

As used herein, the term "heteroatom" includes oxygen (O), nitrogen (N), sulfur (S) and silicon (Si).

I. B. Introduction

This invention provides fertilizer compositions, methods of making these compositions, and methods of using these compositions.

II. Fertilizer Concentrate

The present invention provides fertilizer concentrate compositions. The fertilizer concentrate comprises a dithiocarbamate, at least one phosphite salt, and is essentially devoid of dispersants or wetting agents. The fertilizer concentrate compositions can be provided in liquid or solid form. These compositions can further comprise organic acids, sulfur compounds, thickeners, humectants, antimicrobials, pesticides, herbicides, plant growth regulators, boron compounds, additional fungicides and diluents.

II. A. Dithiocarbamate

Dithiocarbamates can be used in the invention for one of several purposes. First, dithiocarbamates comprise sulfur and can thus supply this nutrient to the plant. In addition, most dithiocarbamates, such as mancozeb, maneb, metiram and zaneb comprise zinc and can thus supply this nutrient to the plant. Some dithiocarbamates, such as mancozeb, comprise other nutrients such as magnesium and can thus supply these nutrients to the plant. Finally, dithiocarbamates are widely used as contact fungicides and can thus aid in plant growth by retarding the spread of deleterious organisms. Examples of these deleterious organisms include *Septoria* sp., *Botrytis* sp., *Anthracnose* sp., and mildew fungi.

In an exemplary embodiment, the fertilizer concentrate comprises a dithiocarbamate. The amount of dithiocarbamate used in the fertilizer concentrate is about 0.125 kg of dithiocarbamate/kg of fertilizer concentrate or greater. In another exemplary embodiment, the amount of dithiocarbamate used in the fertilizer concentrate is between about 0.125 kg/kg to about 1 kg/kg. In yet another exemplary embodiment, the amount of dithiocarbamate used in the fertilizer concentrate is between about 0.125 kg/kg to about 0.85 kg/kg. In yet another exemplary embodiment, the amount of dithiocarbamate used in the fertilizer concentrate is between about 0.5 kg/kg to about 0.9 kg/kg. In another exemplary embodiment, the amount of dithiocarbamate used in the fertilizer concentrate is between about 0.6 kg/kg to about 0.9 kg/kg. In another exemplary embodiment, the amount of dithiocarbamate used in the fertilizer concentrate is between about 0.3 kg/kg to about 0.7 kg/kg. In still another exemplary embodiment, the amount of dithiocarbamate used in the fertilizer concentrate is between about 0.55 kg/kg to about 0.95 kg/kg. In yet another exemplary embodiment, the amount of dithiocarbamate used in the fertilizer concentrate is between about 0.1 5 kg/kg to about 0.5 kg/kg.

II. B. Phosphite Salt

Phosphite ($HPO_3$) is used in the invention to supply phosphorus to the plant. The use of phosphite confers several advantages.

First, unlike sulfate and phosphate, phosphite is readily absorbed by the leaves. Because of this, phosphite can be an excellent fertilizer material for use in foliar applications.

Second, unlike phosphates, phosphite has greater soil solubility and is not immobilized rapidly in the soil. As such, phosphite readily moves to the roots and is absorbed by the plant. Because of this, phosphite is an excellent stable, slow release fertilizer material for use in soil and plant applications.

Phosphite can be present in salt form with a variety of different counterions. Examples of these counterions include potassium, sodium, calcium, and magnesium. A more complete list of suitable counterions is provided in U.S. Pat. No. 5,514,200, the disclosure of which is herein incorporated by reference.

In an exemplary embodiment, the fertilizer concentrate comprises a phosphite salt. The amount of phosphite salt used in the fertilizer concentrate is about 0.005 kg of phosphite salt/kg of fertilizer concentrate or greater. In another exemplary embodiment, the amount of phosphite salt used in the fertilizer concentrate is between about 0.005 kg/kg to about 0.5 kg/kg. In yet another exemplary embodiment, the amount of phosphite salt used in the fertilizer concentrate is between about 0.01 kg/kg to about 0.5 kg/kg. In yet another exemplary embodiment, the amount of phosphite salt used in the fertilizer concentrate is between about 0.05 kg/kg to about 0.4 kg/kg. In another exemplary embodiment, the amount of phosphite salt used in the fertilizer concentrate is between about 0.1 kg/kg to about 0.45 kg/kg. In another exemplary embodiment, the amount of phosphite salt used in the fertilizer concentrate is between about 0.125 kg/kg to about 0.3 kg/kg. In still another exemplary embodiment, the amount of phosphite salt used in the fertilizer concentrate is between about 0.2 kg/kg to about 0.35 kg/kg. In yet another exemplary embodiment, the amount of phosphite salt used in the fertilizer concentrate is between about 0.25 kg/kg to about 0.4 kg/kg.

II. C. Phosphorus-Containing Acid and Deprotonating Bases

Phosphorus-containing acids can be used in the fertilizer concentrate. Examples of phosphorus-containing acids include phosphoric acid, phosphorous acid, hypophosphorous acid, polyphosphorous acid, polyhypophosphorous acid, and combinations thereof. Phosphorus-containing acids can be useful in the invention as they maintain the buffering capacity of the solution. In addition, deprotonating bases can be also be utilized in the invention in order to maintain the buffering capacity of the solution. Examples of deprotonating bases include potassium hydroxide, calcium hydroxide, sodium hydroxide, and ammonium hydroxide.

In an exemplary embodiment, the amount of phosphorus-containing acids used in the fertilizer concentrate is about 0.008 kg of phosphorus-containing acid/kg of fertilizer concentrate. In another exemplary embodiment, the amount of phosphorus-containing acids used in the fertilizer concentrate is between about 0.008 kg/kg to about 0.3 kg/kg. In yet another exemplary embodiment, the amount of phosphorus-containing acids used in the fertilizer concentrate is between about 0.01 kg/kg to about 0.1 kg/kg. In yet another exemplary embodiment, the amount of phosphorus-containing acids used in the fertilizer concentrate is between about 0.1 kg/kg to about 0.3 kg/kg. In yet another exemplary embodiment, the amount of phosphorus-containing acids used in the fertilizer concentrate is between about 0.1 kg/kg to about 0.3 kg/kg. In yet another exemplary embodiment, the amount of phosphorus-containing acids used in the fertilizer concentrate is between about 0.05 kg/kg to about 0.2 kg/kg.

In an exemplary embodiment, the amount of the inorganic base used in the fertilizer concentrate is between about 0.008 kg of inorganic base/kg of fertilizer concentrate to about 0.2 kg/kg. In yet another exemplary embodiment, the amount of the inorganic base used in the fertilizer concentrate is between about 0.01 kg/kg to about 0.1 kg/kg. In yet another exemplary embodiment, the amount of the inorganic base used in the fertilizer concentrate is between about 0.1 kg/kg to about 0.2 kg/kg. In yet another exemplary embodiment, the amount of the inorganic base used in the fertilizer concentrate is between about 0.05 kg/kg to about 0.15 kg/kg. In yet another exemplary embodiment, the amount of the inorganic base used in the fertilizer concentrate is between about 0.05 kg/kg to about 0.2 kg/kg.

II. D. Organic acids

Organic acids can be useful in the invention in several ways. First, organic acids can increase the solubility of the phosphite salt in the fertilizer compositions. Second, organic acids can act as anti-oxidants and slow the oxidation of phosphite to phosphate which can occur due to abiotic and biotic factors such as temperature, sunlight, aeration, and chemical oxidants in the spray tank. Organic acids of use in the invention include monocarboxylic acids, dicarboxylic acids, tricarboxylic acids and higher molecular weight carboxylic acids such as polymalic acid. Other organic acids of use in the invention include amino acids (such as aspartic acid, glutamic acid, serine threonine and cysteine), and fatty acids (including both saturated acids such as lauric, myristic, stearic, and arachidic acids, as well as unsaturated acids such as oleic, linoleic, cinnamic, linolenis, eleostearic, and arachidonic acids). Additional examples of organic acids include phenol and toluene sulfonic acid. Carboxylic acids of the invention contain substituted or unsubstituted alkyl, substituted or unsubstituted cycloalkyl, substituted or unsubstituted heteroalkyl, substituted or unsubstituted heterocycloalkyl, substituted or unsubstituted aryl, and substituted or unsubstituted heteroaryl moieties. Monocarboxylic acids which can be used in the fertilizer concentrate include methanoic(formic) acid, ethanoic(acetic)acid, propanoic(propionic)acid, and butanoic(butyric)acid. Dicarboxylic acids which can be used in the fertilizer concentrate include ethanedioic(oxalic)acid, propanedioic(malonic)acid, butanedioic(succinic)acid, pentanedioic(glutaric)acid, hexanedioic(adipic)acid, heptanedioic(pimelic)acid, cis-2-butenedioic(malic)acid, trans-2-butenedioic(fumaric)acid, benzene-1,2 dicarboxylic (phthalic)acid, benzene-1,3 dicarboxylic(isophthalic)acid, and benzene-1,4 dicarboxylic(terephthalic)acid, tartaric acid, and 2,3 dihydroxylated succinic acid. Tricarboxylic acids which can be used in the fertilizer concentrate include citric acid as well as α-keto acids.

In an exemplary embodiment, the organic acid used in the fertilizer concentrate is citric acid. In another exemplary embodiment, the organic acid used is maleic acid. In yet another exemplary embodiment, more than one organic acid is used.

In an exemplary embodiment, the amount of organic acid used in the fertilizer concentrate is between about 0.005 kg of organic acid/kg of fertilizer concentrate to about 0.2 kg/kg. In another exemplary embodiment, the amount of organic acid used in the fertilizer concentrate is between about 0.005 kg/kg to about 0.05 kg/kg. In yet another exemplary embodiment, the amount of organic acid used in the fertilizer concentrate is between about 0.01 kg/kg to about 0.2 kg/kg. In yet another exemplary embodiment, the amount of organic acid used in the fertilizer concentrate is between about 0.01 kg/kg to about 0.1 kg/kg. In yet another exemplary embodiment, the amount of organic acid used in the fertilizer concentrate is between about 0.1 kg/kg to about 0.2 kg/kg. In yet another exemplary embodiment, the amount of organic acid used in the fertilizer concentrate is between about 0.05 kg/kg to about 0.15 kg/kg.

In another exemplary embodiment, the invention is a multiple buffered dithiocarbamate and phosphorus containing fertilizer concentrate. This fertilizer concentrate can comprise a first buffer system comprising a phosphorous acid and a salt of a phosphorous acid and a second buffer system comprising an organic acid and a salt of an organic acid. The organic acid in this fertilizer concentrate is present in an amount of about 0.02 kg/kg or greater. In another exemplary embodiment, the fertilizer concentrate comprises two buffering systems. In yet another exemplary embodiment, when the fertilizer concentrate is diluted with water, there is formed a ready-to-use fertilizer having a foliage-acceptable pH for sulfur, zinc and phosphorus uptake.

II. E. Sulfur Compounds

In another aspect of the invention, the fertilizer composition further comprises a sulfur compound. Sulfur compounds are advantageous as plant nutrients. As a macro nutrient, sulfur is an important constituent in protein structure, as well as in nitrogen metabolism.

In an exemplary embodiment, the sulfur compound is a member selected from sulfates, sulfides, sulfites, and organosulfur. In another exemplary embodiment, the sulfur compound is a sulfone. In yet another exemplary embodiment, the sulfur compound is dimethyl sulfone. In yet another exemplary embodiment, the sulfur compound is a sulfoxide.

In an exemplary embodiment, the amount of the sulfur compound used in the fertilizer concentrate is between about 0.005 kg of sulfur compound/kg of fertilizer concentrate to about 0.2 kg/kg. In another exemplary embodiment, the amount of the sulfur compound used in the fertilizer concentrate is between about 0.005 kg/kg to about 0.05 kg/kg. In yet another exemplary embodiment, the amount of the sulfur compound used in the fertilizer concentrate is between about 0.01 kg/kg to about 0.2 kg/kg. In yet another exemplary embodiment, the amount of the sulfur compound used in the fertilizer concentrate is between about 0.01 kg/kg to about 0.1 kg/kg. In yet another exemplary embodiment, the amount of the sulfur compound used in the fertilizer concentrate is between about 0.1 kg/kg to about 0.2 kg/kg. In yet another exemplary embodiment, the amount of the sulfur compound used in the fertilizer concentrate is between about 0.05 kg/kg to about 0.15 kg/kg.

II. F. Thickener/Suspending Agent/Stabilizing Agent/Viscosity-Increasing Agent/Binding Agent In another aspect of the invention, the fertilizer composition further comprises a thickener. Thickeners can provide the benefits of controlling solution viscosity as well as enabling higher concentrations of the dithiocarbamates and phosphite salts to be maintained in a suspension.

In an exemplary embodiment, the thickener is a polymeric deposition agent. Examples of these include, but are not limited to, cellulose, starch, polyarcylamides or their copolymers or derivatives, polymers and copolymers of acrylic acid and methacrylic acid or their salts, polymethacrylamides or their copolymers or derivatives, polyacrylonitriles, their hydrolysis products, copolymers, polyvinyl polymers, copolymers, or derivatives.

In another exemplary embodiment, the thickener is a natural gum. Examples of these include, but are not limited to, gums, such as (arabic, acacia, furcelleran, tragacanth, ghatti, guar, karaya, locust bean, and xanthum. These gums can be incorporated in their derivatized, non-derivatized, cationic, and non-cationic versions.

In another exemplary embodiment, the thickener is an oil or oil substitute. Examples of these include, but are not limited to, alkylated fatty acid esters, alkylated natural oils, hydrocarbon oils, and fatty acids.

Alkylated fatty acid esters include, but are not limited to, methylated fatty acids, ethylated fatty acids, and butylated fatty acids. Methylated fatty acids include, but are not limited to, methylated $C_{6-19}$ fatty acids, methylated tall oil fatty acids, methylated oleic acid, methylated linoleic acid, methylated linolenic acid, methylated stearic acid, methylated palmitic acid, and blends thereof. Ethylated fatty acids include, but are not limited to, ethylated $C_{6-19}$ fatty acids, ethylated tall oil fatty acids, ethylated oleic acid, ethylated linoleic acid, ethylated linolenic acid, ethylated stearic acid, ethylated palmitic acid, and blends thereof. Butylated fatty acids include, but are not limited to, butylated $C_{6-19}$ fatty acids, butylated tall oil fatty acids, butylated oleic acid, butylated linoleic acid butylated linolenic acid, butylated stearic acid, butylated palmitic acid, and blends thereof.

Alkylated natural oils include, but are not limited to, alkylated soybean oil, alkylated canola oil, alkylated coconut oil, and alkylated sunflower oil. Alkylated soybean oils include, but are not limited to, methylated soybean oil, ethylated soybean oil, butylated soybean oil, and blends thereof. Alkylated canola oil include, but are not limited to, methylated canola oil, ethylated canola oil, butylated canola oil, and blends thereof. Alkylated coconut oils include, but are not limited to, methylated coconut oil, ethylated coconut oil, butylated coconut oil, and blends thereof. Alkylated sunflower oil include, but are not limited to, methylated sunflower oil, ethylated sunflower oil, butylated sunflower oil, and blends thereof.

Hydrocarbon oils include, but are not limited to, mineral oils including, but not limited to, paraffinic mineral oils, naphthenic mineral oils, aromatic mineral oils, and blends thereof. Vegetable oils include, but are not limited to, soybean oil, canola oil, cottonseed oil, and blends thereof. Fatty acids include, but are not limited to, $C_6$-$C_{19}$ fatty acids, tall oil fatty acids, oleic acid, linoleic acid, linolenic acid, stearic acid, palmitic acid, and blends thereof. Epoxified seed oils, polybutenes, and silicon containing thickeners, such as precipitated silicas or precipitated silicates can also be used as thickeners in the invention.

The oil can contain at least one of the above oils or its equivalent. The oil can also be a blend of at least two oils. When an oil is used, a surfactant or emulsifier must also be used if the composition is intended for aqueous based sprays.

Additional examples of thickeners include carboxymethylcellulose, carrageenan, carbomer-940 A, carbomer-956, alginate (propylene glycol alginate), casein (sodium caseinate), gelatin, mannitol, and sorbitol.

In an exemplary embodiment, the amount of thickener used in the fertilizer concentrate is between about 0.0001 kg of thickener/kg of fertilizer concentrate to about 0.1 kg/kg. In another exemplary embodiment, the amount of thickener used in the fertilizer concentrate is between about 0.001 kg/kg to about 0.1 kg/kg. In yet another exemplary embodiment, the amount of thickener used in the fertilizer concentrate is between about 0.001 kg/kg to about 0.05 kg/kg. In yet another exemplary embodiment, the amount of thickener used in the fertilizer concentrate is between about 0.05 kg/kg to about 0.1 kg/kg. In yet another exemplary embodiment, the amount of thickener used in the fertilizer concentrate is between about 0.03 kg/kg to about 0.08 kg/kg.

II. G. Humectants

In another aspect of the invention, the fertilizer composition further comprises a humectant. Humectants can provide the benefit of promoting retention and absorption of moisture in a fertilizer. Since humectants absorb water from the air, the addition of a humectant has the effect of preventing the fertilizer from drying out after application and also in rehydration, when the relative humidity goes up (such as at night) particularly in arid climates.

Examples of humectants of use in the invention include aliphatic polyhydric alcohols and sugar alcohols, and salts thereof, such as macrogol, propane diol, polyethylene glycol, diglycerol, propylene glycol, polypropylene glycol, butylene glycol, polybutylene glycol, dipropylene glycol, glycerin, glycerol, sorbitol, sodium pyrrolidone carboxylate, ethyl carbitol, D-xylitol, polysorbate 60, 65 or 80 and hyaluronic acid can also be incorporated into the invention.

In an exemplary embodiment, the amount of humectant used in the fertilizer concentrate is between about 0.0005 kg of humectant/kg of fertilizer concentrate to about 0.2 kg/kg. In another exemplary embodiment, the amount of humectant used in the fertilizer concentrate is between about 0.001 kg/kg to about 0.1 kg/kg. In yet another exemplary embodiment, the amount of humectant used in the fertilizer concentrate is between about 0.01 kg/kg to about 0.1 kg/kg. In yet another exemplary embodiment, the amount of humectant used in the fertilizer concentrate is between about 0.05 kg/kg to about 0.1 kg/kg. In yet another exemplary embodiment, the amount of humectant used in the fertilizer concentrate is between about 0.01 kg/kg to about 0.05 kg/kg. In yet another exemplary embodiment, the amount of humectant used in the fertilizer concentrate is between about 0.03 kg/kg to about 0.08 kg/kg.

II. H. Antimicrobials

In another aspect of the invention, the fertilizer composition further comprises an antimicrobial. Antimicrobials are useful since they can retard the growth of microorganisms which may degrade a formulated product.

Examples of antimicrobial agents include quinolone carboxylic acids, nitrofurans, sulfonamides, benzoic acid derivatives, sulfites, oxyhalide comopunds, and metallic salts (such as silver, copper, and magnesium). Quinolone carboxylic acids include ciproflaxin, nalidixic acid, cinoxacin, norfloxacin, enoxacin, pefloxacin, iomefloxacin, fleroxacin, sparfloxacin, refloxacin, temafloxacin, amifloxacin, irloxacin and piromidic acid. Nitrofurans include furum, flirazolidone, Z-furan, furylfuramide, nitrovin, furalazine, acetylfuratrizine, panfuran—S, nifuroxime, nitrofurazone, nifuraldezone, nihydrazone, nitrofurantoin, nifuratel, nitrofurathiazide, nifurtoinol, nifrirtoinol. Sulfonamides include N-acylsulfanilamides, N-heterocyclic—N-acylsulfanilamides, and N-heterocyclic—N-acetylsulfanilamides.

Additional examples of antimicrobials include benzalkonium chloride, photosensitive element No. 201, a chlorhexidine gluconate solution, chloroxylenol, trichlorocarbanilide, halocarvan, mononitroguaiacol, cephalosporin, 1,2-benziisothiazoline-3-one.

In an exemplary embodiment, the amount of antimicrobial used in the fertilizer concentrate is between about 0.00005 kg of antimicrobial/kg of fertilizer concentrate to about 0.1 kg/kg. In another exemplary embodiment, the amount of antimicrobial used in the fertilizer concentrate is between about 0.0005 kg/kg to about 0.05 kg/kg. In yet another exemplary embodiment, the amount of antimicrobial used in the fertilizer concentrate is between about 0.005 kg/kg to about 0.05 kg/kg. In yet another exemplary embodiment, the amount of antimicrobial used in the fertilizer concentrate is between about 0.0005 kg/kg to about 0.005 kg/kg. In yet another exemplary embodiment, the amount of antimicrobial used in the fertilizer concentrate is between about 0.005 kg/kg to about 0.05 kg/kg. In yet another exemplary embodiment, the amount of antimicrobial used in the fertilizer concentrate is between about 0.001 kg/kg to about 0.03 kg/kg.

II. I. Pesticides

In another aspect of the invention, the fertilizer compositions of the invention further comprise a pesticide. Examples of pesticides include organophosphates, carbamates, insect growth regulators, and naturally derived insecticides. An example of a naturally derived insecticide is garlic oil.

In an exemplary embodiment, the amount of pesticide used in the fertilizer concentrate is between about 0.0008 kg of pesticide/kg of fertilizer concentrate to about 0.7 kg/kg. In another exemplary embodiment, the amount of pesticide used in the fertilizer concentrate is between about 0.01 kg/kg to about 0.6 kg/kg. In yet another exemplary embodiment, the amount of pesticide used in the fertilizer concentrate is between about 0.05 kg/kg to about 0.3 kg/kg. In yet another exemplary embodiment, the amount of pesticide used in the fertilizer concentrate is between about 0.1 kg/kg to about 0.3 kg/kg. In yet another exemplary embodiment, the amount of pesticide used in the fertilizer concentrate is between about 0.3 kg/kg to about 0.6 kg/kg.

II. J. Herbicides

In another aspect of the invention, the fertilizer composition of the invention further comprises a herbicide. Examples of herbicides include hormonal-based herbicides, pre-emergent herbicides, as well as post-emergent, or contact, herbicides. Examples of pre-emergent herbicides include sulfonyl ureas. Examples of post-emergent herbicides include glyphosate, paraquat, and 2,4 D.

In an exemplary embodiment, the amount of herbicide used in the fertilizer concentrate is between about 0.0008 kg of herbicide/kg of fertilizer concentrate to about 0.7 kg/kg. In another exemplary embodiment, the amount of herbicide used in the fertilizer concentrate is between about 0.01 kg/kg to about 0.6 kg/kg. In yet another exemplary embodiment, the amount of herbicide used in the fertilizer concentrate is between about 0.05 kg/kg to about 0.3 kg/kg. In yet another exemplary embodiment, the amount of herbicide used in the fertilizer concentrate is between about 0.1 kg/kg to about 0.3 kg/kg. In yet another exemplary embodiment, the amount of herbicide used in the fertilizer concentrate is between about 0.3 kg/kg to about 0.6 kg/kg.

II. K. Plant Growth Regulators/Hormones

In another aspect of the invention, the fertilizer composition of the invention further comprises a plant growth regulator. Plant growth regulators may be synthetic compounds (e.g., IBA and Cycocel) that mimic naturally occurring plant hormones, or they may be natural hormones that were extracted from plant tissue (e.g., IAA).

There are several groups of plant-growth-regulating compounds, including auxins, gibberellins (GA), cytokinins, ethylene, abscisic acid (ABA), brassinolides, and jasmonates. For the most part, each group contains both naturally occurring hormones and synthetic substances.

Auxin causes several responses in plants, primarily affecting cell elongation. These responses include phototropism (bending toward a light source), geotropism (downward root growth in response to gravity), promotion of apical dominance, flower formation, fruit set and growth, and the formation of adventitious roots. In practice, auxins are the active ingredient in most rooting compounds in which cuttings are dipped during vegetative propagation. Examples of auxins include indoleacetic acid (IAA) which is synthesized from tryptophan, as well as indolebutyric acid (IBA), as well as synthetic derivatives of auxins.

Gibberellins also cause several responses in plants, including stimulation of cell division and elongation, termination of seed dormancy, and acceleration of germination. They stimulate RNA to promote synthesis of enzymes that convert stored nutrients (starches) to sugars needed for rapid cell respiration during germination. Gibberellins often work with auxins to achieve their effects. Examples of gibberellins include gibberellic acids with carbon chains ranging in length from four to twelve carbons.

Cytokinins are a group of phenyl urea derivatives of adenine. Unlike other plant growth regulators, cytokinins are found in both plants and animals. They stimulate cytokinesis, or cell division, as well as delay aging and senescence. Examples of cytokinins include zeatin.

Ethylene is unique in that it is found only in the gaseous form. It induces ripening, causes leaves to droop (epinasty) and drop (abscission), and promotes senescence. Plants often increase ethylene production in response to stress, and ethylene often is found in high concentrations within cells at the end of a plant's life. Ethylene also is used to ripen fruit (e.g., green bananas).

Abscisic acid (ABA) is a general plant-growth inhibitor. It induces dormancy and prevents seeds from germinating; causes abscission of leaves, fruits, and flowers; and causes stomata to close. High concentrations of ABA in guard cells during periods of drought stress probably play a role in stomatal closure.

In an exemplary embodiment, the amount of plant growth regulator used in the fertilizer concentrate is between about 0.0005 kg of plant growth regulator/kg of fertilizer concentrate to about 0.2 kg/kg. In an exemplary embodiment, the amount of plant growth regulator used in the fertilizer concentrate is between about 0.0005.kg/kg to about 0.1 kg/kg. In another exemplary embodiment, the amount of plant growth regulator used in the fertilizer concentrate is between about 0.001 kg/kg to about 0.1 kg/kg. In yet another exemplary embodiment, the amount of plant growth regulator used in the fertilizer concentrate is between about 0.1 kg/kg to about 0.1 kg/kg. In yet another exemplary embodiment, the amount of plant growth regulator used in the fertilizer concentrate is between about 0.5 kg/kg to about 0.1 kg/kg. In yet another exemplary embodiment, the amount of plant growth regulator used in the fertilizer concentrate is between about 0.1 kg/kg to about 0.05 kg/kg. In yet another exemplary embodiment, the amount of plant growth regulator used in the fertilizer concentrate is between about 0.03 kg/kg to about 0.08 kg/kg.

II. L. Boron Compounds

Though classified as a micronutrient, a lack of boron (B) in a plant diet will affect growth the same as a lack of a primary nutrient such as nitrogen. Boron regulates the transport of sugars through membranes, cell division, cell development, and auxin metabolism. Boron deficiency is often manifested with the failure to produce seeds or fruits. It is the most widespread of all micronutrient deficiencies in the Pacific Northwest. Examples of boron compounds useful in the invention include boric acid ($H_3BO_3$); borax or disodium borate decahydrate ($Na_2B_4O_7 \cdot 10H_2O$); borated gypsum, or calcium sulfate dihydrate disodium borate ($CaSO_4$, $2\ H_2O$+ $Na_2B_4O_7$); Fertilizer Borate 48, or disodium borate hexahydrate ($Na_2B_4O_7 \cdot 5H_2O$); Fertilizer Borate 68, or disodium borate ($Na_2B_4O_7$); Solubor, or disodium borate hexahydrate and disodium borate decahydrate ($Na_2B_4O_7 \cdot 5H_2O$+ $Na_2B_{10}O_{16} \cdot 10H_2O$). Borax and borated gypsum are often used in solid compositions of boron fertilizers. Boric acid and disodium borate hexahydrate and disodium borate decahydrate can be used for either soil or foliar application.

In an exemplary embodiment, the amount of the boron compound used in the fertilizer concentrate is between about 0.0001 kg of boron compound/kg of fertilizer concentrate to about 0.1 kg/kg. In another exemplary embodiment, the amount of the boron compound used in the fertilizer concentrate is between about 0.001 kg/kg to about 0.1 kg/kg. In yet another exemplary embodiment, the amount of the boron compound used in the fertilizer concentrate is between about 0.001 kg/kg to about 0.05 kg/kg. In yet another exemplary embodiment, the amount of the boron compound used in the fertilizer concentrate is between about 0.05 kg/kg to about 0.1 kg/kg. In yet another exemplary embodiment, the amount of the boron compound used in the fertilizer concentrate is between about 0.03 kg/kg to about 0.08 kg/kg.

II. M. Plant Nutrient Compounds

In order to provide additional nutrients to the plant, the compositions of the invention can further comprise one or more additional plant nutrients. These can be primary nutrients, such as nitrogen or potassium. The plant nutrients can also be secondary nutrients such as magnesium and sodium. Finally the plant nutrients can also be micronutrients such as cobalt, copper, iron, manganese, molybdenum, and zinc.

II. N. Additional Fungicide

In another aspect of the invention, the fertilizer compositions of the invention further comprise an additional fungicide. Examples of an additional fungicide include a dithiocarbamate fungicide that differs from the first fungicide, copper-containing flugicides such as oxychloride, oxysulphate, (tetrahydro)phthalimides (captan, captafol, folpel), triazole fungicides such as propiconazole, tebuconazole, and myclobutanil, thiophanate-methyl, N-(1-butyl carbamoyl)-2-benzimidazole, methyl carbamate (benomyl), 1,2-di-(3-methoxy or ethoxy)carbonyl-2-thioureido benzenes (thiophanates), methyl 2-benzimidazole carbamate, strobilurins A-H, dithianone, cymoxanil, fenarimol, chlorothalonil, and combinations thereof. Chlorothalonil is amendable to free flow packaging, which means that they are easy to measure and mix with water. Also, most formulations of chlorothalonil can be tank-mixed with insecticides so that a "piggyback" application containing both the fungicide and insecticide can be made at the same time.

The fertilizer compositions of the invention may also be mixed with other fungicidal, anti-mildew phosphorus derivatives, especially 2-hydroxy-1,3,2-dioxaphospholanes and β-hydroxy ethyl phosphites.

In an exemplary embodiment, the amount of an additional fungicide used in the fertilizer concentrate is between about 0.08 kg of an additional fungicide/kg of fertilizer concentrate to about 0.7 kg/kg. In another exemplary embodiment, the amount of an additional fungicide used in the fertilizer concentrate is between about 0.01 kg/kg to about 0.6 kg/kg. In yet another exemplary embodiment, the amount of an additional fungicide used in the fertilizer concentrate is between about 0.05 kg/kg to about 0.3 kg/kg. In yet another exemplary embodiment, the amount of an additional fungicide used in the fertilizer concentrate is between about 0.1 kg/kg to about 0.3 kg/kg. In yet another exemplary embodiment, the amount of an additional fungicide used in the fertilizer concentrate is between about 0.1 kg/kg to about 0.2 kg/kg. In yet another exemplary embodiment, the amount of an additional fungicide used in the fertilizer concentrate is between about 0.15 kg/kg to about 0.25 kg/kg. In yet another exemplary embodiment, the amount of an additional fungicide used in the fertilizer concentrate is between about 0.3 kg/kg to about 0.6 kg/kg.

II. O. Granule Size

The compositions of the invention can be formed into granules. In an exemplary embodiment, the granules have a diameter between about 0.001 mm and about 0.5 mm. In an exemplary embodiment, the granules have a diameter between about 0.005 mm and about 0.1 mm. In an exemplary embodiment, the granules have a diameter between about 5 microns and about 100 microns. In an exemplary embodiment, the granules have a diameter between about 5 microns and about 100 microns. In an exemplary embodiment, the granules have a diameter between about 5 microns and about 50 microns.

In another exemplary embodiment, at least about 90% of the granules in the composition have a diameter within the parameters described above. In another exemplary embodiment, at least about 80% of the granules in the composition have a diameter within the parameters described above. In another exemplary embodiment, at least about 70% of the granules in the composition have a diameter within the parameters described above. In another exemplary embodiment, at least about 60% of the granules in the composition have a diameter within the parameters described above.

The granules of the invention can be made in a variety of ways. The preparation of these granules is generally carried out starting with powders which have the same chemical composition as the fertilizer compositions according to the invention, and then these powders are moistened, shaped and finally dried.

To obtain powders according to the invention, the active substance, or active substances, are intimately mixed in suitable mixers with additional substances, and, if appropriate, the porous vehicle is impregnated with them, and everything is ground on mills or other suitable grinders. For example, constituents of the various compositions can be passed through a hammer mill which has a grating of about 0.5 mm mesh for breaking up the lumps. In this way, a powder is obtained which contains particles of a size between about 5 and about 50 microns.

According to a first preparation method for the granules according to the invention, the powders are moistened by directly adding liquid water (from about 1 to about 20% of water, preferably about 10 to about 18% of water), and this moistened powder, which has the consistency of a dough, is extruded through a grill or perforated plate in such a way as to obtain an extrudate in the form of a large number of elongated cylinders, which are sometimes named rolls or even spaghetti, which are subsequently broken up lengthwise in such a way as to produce a large number of small short cylinders which constitute the granules according to the invention. These are moist and only need drying (for example more than about 80° C., preferably more than about 100° C., in a ventilated atmosphere) to obtain proper granules according to the invention which can be marketed. For example, the compositions can be shaped into granules by extrusion. In a mixer/beater, 500 g of powder are moistened with 15% of water for about 5 minutes. The powder is then continuously extruded with the aid of a perforated-roll extruder (openings of diameter: 1.5 mm). The moist granules which have thus been formed are dried in a fluidized bed in which the temperature of the air which enters is 100° C., and then the mixture is sieved in such a way as to obtain granules of a size of between 0.5 and 1.6 mm, on average of about 1.5 mm.

In a second preparation method for the granules according to the invention, the powders are moistened by being sprayed with water (from 5 to 35% of water, preferably 20 to 30% of water) in a fluidized bed formed with the powder. This operation leads directly to the formation of moist granules, and it is therefore only necessary to dry them to obtain the proper granules according to the invention which can be marketed. For example, the compositions were shaped into granules by the fluidized-bed technique. 500 g of homogenized powder are fluidized in a fluidized-bed granulator. Agglomeration is obtained by spraying 25% of water onto the powder bed at ambient temperature. The granules formed are then dried by raising the temperature of the air which enters to 100° C., and then the mixture is sieved as above, and granules of a similar size are obtained.

According to a third preparation method for the granules according to the invention, the powders are moistened by direct spraying of liquid water (from 1 to 20% of water, preferably 10 to 18% of water) onto the powder which is located on an inclined and rotating plate. The fact that this plate rotates allows the powder grains to remain dissociated from one another. The spraying of water onto these grains during the movement also leads to the formation of moist granules which then only need drying (for example at more than 80° C., preferably at 100° C., in a ventilated atmosphere) so as to obtain the proper granules according to the invention which can be marketed.

According to a fourth preparation method for the granules according to the invention (named atomization), a concentrated suspension is prepared from a powder, by directly adding liquid water (from 20 to 70% of water, preferably 30 to 50% of water); this suspension is then sprayed in a dryer with hot air (atomizer) which allows fine and dry granules to be obtained by rapid evaporation of the water contained in the droplets of suspension; the temperature of the drying air is generally between 120 and 300° C., preferably between 150 and 250° C. For example, the compositions were shaped into granules by atomization. 600 g of powder are dispersed in 400 g of water in such a way as to constitute a suspension which is sprayed in a jet atomizer where the temperature of the air at the inlet is 180° C. and the temperature of the air at the outlet is 90° C. Granules of a size between 0.1 and 0.4 mm are obtained.

III. Ready-to-Use Fertilizers

The present invention also provides ready-to-use fertilizer compositions. A ready-to-use fertilizer comprises a fertilizer concentrate and a diluent. This ready-to-use fertilizer composition can be provided in either liquid or solid form. Since a ready-to-use fertilizer includes a fertilizer concentrate, the ready-to-use fertilizer also can include any of the components described above, such as organic acids, sulfur compounds, thickeners, humectants, antimicrobials, pesticides, herbicides, plant growth regulators, boron compounds, an additional fungicide and diluents.

IV. Methods of Making the Compositions

The fertilizer concentrates and ready-to-use fertilizers of the invention are prepared by first forming a mixed suspension of a dithiocarbamate and at least one phosphite salt. This suspension can be made either by adding dithiocarbamate and at least one phosphite salt directly to a liquid, or by generating the phosphite salt in situ by adding a phosphite-containing compound with an appropriate counterion-containing compound to a liquid. Agents necessary for maintaining a suspension, such as, humectants, thickeners, etc., can be added with constant stirring. Desired nutrients can also be added with constant stirring. The fertilizers of the invention can also be prepared as solid compositions, identical to the liquid ones by simply leaving out all of the water. The properties are the same as the liquid compositions but have the additional advantage of weighing less for the same amount of nutrient.

V. Methods of Using the Compositions

The fertilizers of the invention are applied according to crop-specific recommendations which will depend upon the application method as well as whether they are applied to the soil or plant. There are several general fertilizer application methods for liquid based fertilizers. The first is application via the irrigation system which can be subdivided into micro, furrow and flood irrigation. To be suitable for irrigation purposes, a fertilizer concentrate will usually be diluted 500 to 10,000 fold. Fruit and vegetable crops are particularly suited for irrigation purposes. The second application method is ground-based, or conventional spraying. This method encompasses application via tractor mounted or powered sprayers, back pack sprayers and electrostatic sprayers. To be suitable for ground-based purposes, a fertilizer concentrate will usually be diluted 10 to 1,000 fold. Fruit and vegetable crops are also suited for ground-based application. The third application method is aerial spraying. To be suitable for aerial purposes, a fertilizer concentrate will usually be diluted 10 to 100 fold. Large acreage crops such as cereals, forage crops and crops grown on plantations, are suited for aerial application. A further fertilizer application method is tree injection, whereby the fertilizer is injected directly into the plant usually in the trunk, scaffold branches or crown roots. Fertilizer applications can also be divided into foliar application, soil application, time of application, rate of application, and product composition. Crops that will benefit from the fertilizers of the invention include, but are not limited to, avocado, citrus, mango, coffee, deciduous tree crops, grapes and other berry crops, soybean and other commercial beans, green vegetables, aliums, asparagus, artichokes, bananas, corn, tomato, cucurbits and cucumis species, lettuce (green vegetables), potato, sugar beets, peppers, sugarcane, hops, tobacco, pineapple, tea, coffee, sisal, cereals and grasses, forage crops, sugar and oil producing crops, forestry, pharmaceutical crops, cotton, ferns, coconut palm and other commercial and ornamental palms, hevea rubber, forage plants and ornamental plants.

In addition to the foliar, soil, and irrigation application methods mentioned above, the present fertilizer may prove beneficial to certain crops through other application methods. For example, trunk paints or other methodologies may provide for a continuous low supply of fertilizers of the invention, such as, for example, "intravenous" feeding. More information can be found at http://www.extension.umn.edu/distribution/horticulture/DG7410.html. In another example, tree injection systems are also encompassed by the invention. In a tree injection system, fertilizer is injected into the trunk or the scaffold of the plant. Tree injection systems are particularly useful for palm trees and other soft stem plants, as well as for the production of bananas. More information on tree injection systems can be found at (http://www.na.fs.fed.us/spfo/pubs/misc/ded/ded.htm).

The invention includes methods of providing dithiocarbamate and phosphorus to a plant. This method comprises mixing water with a fertilizer concentrate, thus forming a ready-to-use fertilizer, and applying this ready-to-use fertilizer to the foliage of a plant. In an exemplary embodiment, the fertilizer concentrate comprises a dithiocarbamate and at least one phosphite salt without the presence of dispersants or wetting agents. In another exemplary embodiment, the fertilizer concentrate can be a suspension. In another exemplary embodiment, the fertilizer concentrate can be a member selected from an aqueous suspension or a non-aqueous suspension.

The invention includes methods of promoting growth in a plant through foliar application of a ready-to-use fertilizer. This method comprises forming a ready-to-use fertilizer through adding water to a fertilizer concentrate, and applying this ready-to-use fertilizer to the foliage of a plant. In an exemplary embodiment, the fertilizer concentrate comprises a dithiocarbamate and at least one phosphite salt without the presence of dispersants or wetting agents. In another exemplary embodiment, the fertilizer concentrate can be a suspension. In another exemplary embodiment, the fertilizer concentrate can be a member selected from an aqueous suspension or a non-aqueous suspension.

The invention includes methods of providing dithiocarbamate and phosphorus to a seed. This method comprises mixing water and a fertilizer concentrate, thus forming a ready-to-use fertilizer that has a seed-acceptable pH for phosphorus uptake, and applying this ready-to-use fertilizer to the seed. In an exemplary embodiment, the fertilizer concentrate comprises a dithiocarbamate and at least one phosphite salt without the presence of dispersants or wetting agents. In another exemplary embodiment, the fertilizer concentrate can be a suspension. In another exemplary embodiment, the fertilizer concentrate can be a member selected from an aqueous suspension or a non-aqueous suspension.

The invention includes methods of preventing the browning of leaves and/or fruit and/or storage organs. This method comprises applying a ready-to-use fertilizer to a plant in an amount sufficient to prevent the browning of its leaves and/or fruit and/or storage organs. In an exemplary embodiment, the ready-to-use fertilizer comprises a fertilizer concentrate and a diluent. In another exemplary embodiment, the fertilizer concentrate comprises a dithiocarbamate and at least one phosphite salt without the presence of dispersants or wetting agents. In another exemplary embodiment, the fertilizer concentrate can be a suspension. In another exemplary embodiment, the fertilizer concentrate can be a member selected from an aqueous suspension or a non-aqueous suspension.

The invention includes slow-release methods of providing a phosphite salt to a plant. This method comprises applying a solid fertilizer concentrate or a solid ready-to-use fertilizer in an amount sufficient to provide phosphite to the plant. In an exemplary embodiment, the fertilizer concentrate comprises a dithiocarbamate and at least one phosphite salt without the presence of dispersants or wetting agents. In another exemplary embodiment, the fertilizer concentrate can be a suspension. In another exemplary embodiment, the fertilizer concentrate can be a member selected from an aqueous suspension or a non-aqueous suspension.

The invention includes methods of extending the shelf-life (i.e. "toughening up") of a plant. This method comprises applying a ready-to-use fertilizer to a plant at a time prior to crop harvest. The time prior to crop harvest can be between twelve hours and seven days. In an exemplary embodiment, the ready-to-use fertilizer comprises a fertilizer concentrate and a diluent. In another exemplary embodiment, the fertilizer concentrate comprises a dithiocarbamate and at least one phosphite salt without the presence of dispersants or wetting agents. In another exemplary embodiment, the fertilizer concentrate can be a suspension. In another exemplary embodiment, the fertilizer concentrate can be a member selected from an aqueous suspension or a non-aqueous suspension.

The invention includes methods of improving the post harvest condition of produce. This method comprises application of a fertilizer of the invention to a plant at a time after crop harvest. This application can take place at a variety of locations, such as in the field immediately after crop harvest, or in a fruit or vegetable packhouse. In an exemplary embodiment, the fertilizer of the invention comprises a fertilizer concentrate. In another exemplary embodiment, the fertilizer concentrate comprises a dithiocarbamate and at least one phosphite salt without the presence of dispersants or wetting agents. In another exemplary embodiment, the fertilizer concentrate can be a suspension. In another exemplary embodiment, the fertilizer concentrate can be a member selected from an aqueous suspension or a non-aqueous suspension.

The invention includes methods of reducing the amount of nitrogen in a tissue of a plant. This method comprises applying a fertilizer of the invention to a plant at a time prior to crop harvest. The time prior to crop harvest can be between twelve hours and fifty days. In another exemplary embodiment, the time prior to crop harvest can be between twelve hours and ten days. In an exemplary embodiment, the fertilizer of the invention comprises a fertilizer concentrate. In another exemplary embodiment, the fertilizer concentrate comprises a dithiocarbamate and at least one phosphite salt without the presence of dispersants or wetting agents. In another exemplary embodiment, the fertilizer concentrate can be a suspension. In another exemplary embodiment, the fertilizer concentrate can be a member selected from an aqueous suspension or a non-aqueous suspension.

The invention includes methods of increasing the amount of manganese or zinc absorbed through the roots of a plant. This method comprises applying a fertilizer of the invention either directly to the roots of a plant, or in the soil surrounding the plant, at a time prior to crop harvest. In an exemplary embodiment, the fertilizer of the invention comprises a fertilizer concentrate. In another exemplary embodiment, the fertilizer concentrate comprises a dithiocarbamate and at least one phosphite salt without the presence of dispersants or wetting agents. In another exemplary embodiment, the fertilizer concentrate can be a suspension. In another exemplary embodiment, the fertilizer concentrate can be a member selected from an aqueous suspension or a non-aqueous suspension.

In order that the invention described herein may be more fully understood, the following examples are set forth. All chemicals used were of analytical reagent quality and approximately 100% by weight unless otherwise specified. All compositions are expressed in terms of weight of calcium phosphite to weight of fertilizer unless otherwise specified. It should be understood that these examples are for illustrative purposes only and are not to be construed as limiting the scope of the invention in any manner.

EXAMPLES

The following examples are provided to illustrate, but not to limit, the compositions and methods of the claimed invention.

Example 1

Solid Formulation of Mancozeb Fertilizer

A fertilizer concentrate was prepared with an NPK analysis of 0-14-9. It was packaged in a one-container system containing (all amounts are kg of ingredient/kg of fertilizer concentrate): 0.75 kg of mancozeb; and 0.25 kg of monopotassium phosphite. This fertilizer concentrate is a solid and was assembled according to the methods described in Section III of this application.

Example 2

Liquid Formulations of Mancozeb Fertilizers

Two liquid fertilizer concentrates were prepared. In one liquid formulation, mancozeb (400 g) plus calcium phosphite (250 g) is mixed with water (300 g) and a suspending agent (50 g). The mixture is a suspension concentrate and is stable. In a second liquid formulation, mancozeb (400 g) plus potassium phosphite (250 g) is mixed with water (300 g) and a suspending agent (50 g). Agglutination occurs in this second liquid formulation.

Figure 2A:
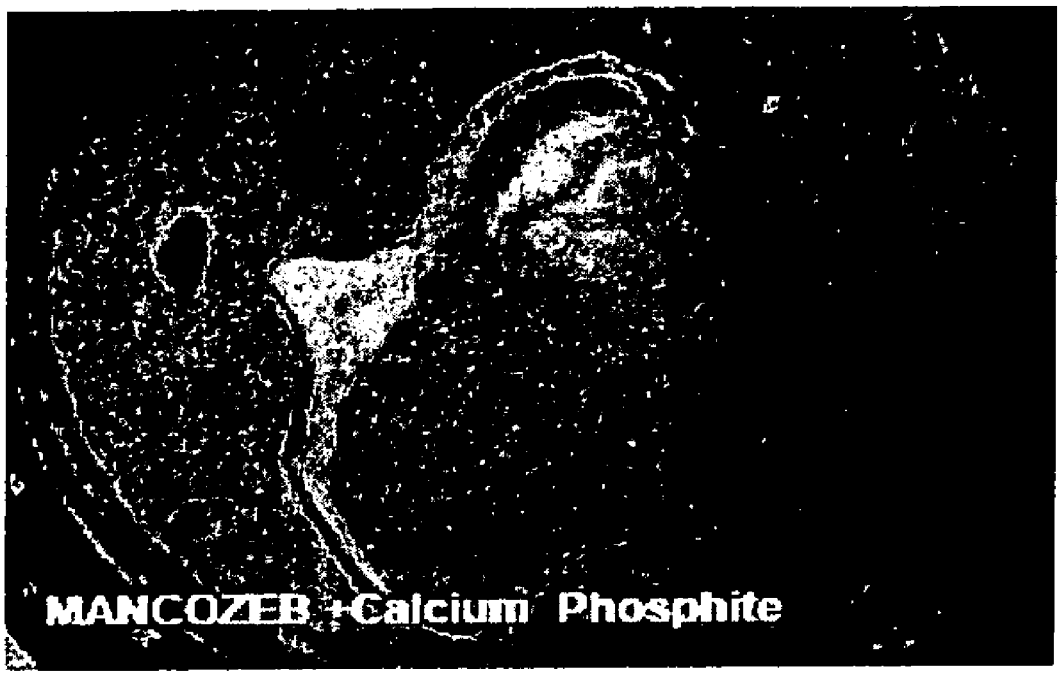
FIG. 2 displays two different mancozeb liquid formulations. The formulation in the upper picture (FIG. 2A) contains 400 g of mancozeb, 250 g of calcium phosphite, 300 g of water and 50 g of a suspending agent. This liquid formulation is stable and forms a flowable liquid formulation. The formulation in the lower picture (FIG. 2B) contains 400 g of mancozeb, 250 g of potassium phosphite, 300 g of water and 50 g of a suspending agent. Agglutination occurs in this liquid formulation.
Figure 2B:
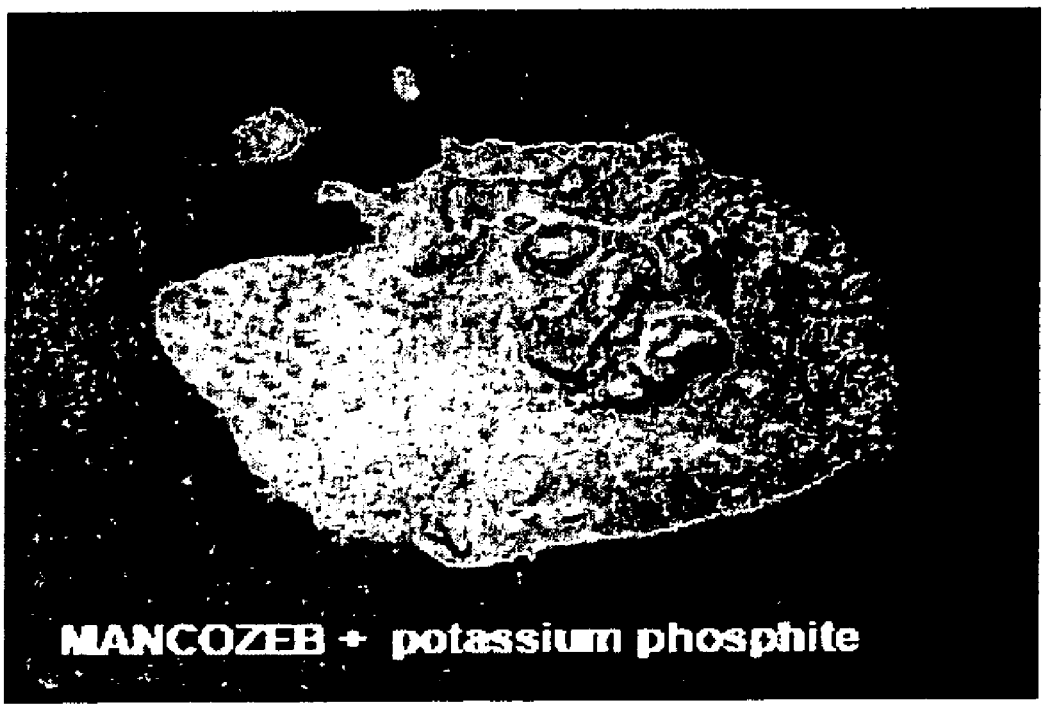

As can be seen from FIG. 2, a liquid formulation of calcium phosphlte in combination with Mancozeb or Maneb results in a stable, not agglutinating formulation. The pH of the formulation was between 7.5 and 9.

Example 3

Spore Germination Tests

The flowable Calcium formulation (named Calciphite) combination plus Mancozeb as described in the above example was tested for its ability to inhibit spore germination as compared to Mancozeb. Water agar plates were prepared and amended with the Calciphite/mancozeb combination (50 ppm) or mancozeb alone (100 ppm). Spores of the fungus Mycosphearella sp at a spore concentration of $4\times10^5$ were sprayed onto the surface of the plates and incubated for 12 hours after which the plates were assessed for germination. The results of these tests are in the following Table:

TABLE

| Treatment | % spore germination |
|---|---|
| Calciphite/mancozeb combination at 50 ppm Mancozeb | 6% |
| Mancozeb at 100 ppm | 81% |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A fertilizer concentrate comprising:
a dithiocarbamate; and
calcium phosphite,
wherein said fertilizer concentrate is essentially devoid of dispersants and wetting agents.

2. The fertilizer concentrate of claim 1, wherein
said dithiocarbamate is in a granular form;
said dithiocarbamate is present in an amount of from about 0.55 kg of dithiocarbamate/kg of fertilizer concentrate to about 0.95 kg of dithiocarbamate/kg of fertilizer concentrate;
said calcium phosphite is present in an amount of from about 0.01 kg of calcium phosphite /kg of fertilizer concentrate to about 0.45 kg of calcium phosphite /kg of fertilizer concentrate.

3. The fertilizer concentrate of claim 2 wherein at least about 90% of the granules of said fertilizer concentrate have a diameter of from about 0.001 mm and about 0.5 mm.

4. The fertilizer concentrate of claim 1, wherein said dithiocarbamate is a member selected from mancozeb, maneb, zineb, thiram and metiram.

5. A method of providing a fertilizer and a fungicide to a plant, said method comprising:
(a) mixing water and the fertilizer of claim 1, thus forming a use-dilution fertilizer; and
(b) applying said use-dilution fertilizer to the foliage of a plant, thus providing said fertilizer and said fungicide to a plant.

6. The fertilizer concentrate of claim 1, wherein
said dithiocarbamate is present in an amount of from about 10% wt of dithiocarbamate/wt of fertilizer concentrate to about 35% wt of dithiocarbamate/wt of fertilizer concentrate;
said calcium phosphite is present in an amount of from about 15% wt of calcium phosphite /wt of fertilizer concentrate to about 35% wt of calcium phosphite /wt of fertilizer concentrate
and-further comprising water in an amount of about 30% wt of water/wt of fertilizer concentrate to about 40% wt of water/wt of fertilizer concentrate.

7. A fertilizer concentrate comprising:
a dithiocarbamate, which is present in an amount of from about 10% wt of dithiocarbamate/wt of fertilizer concentrate to about 35% wt of dithiocarbamate/wt of fertilizer concentrate;
at least one phosphite salt, which is present in an amount of from about 15% wt of phosphite salt/wt of fertilizer concentrate to about 35% wt of phosphite salt/wt of fertilizer concentrate
a suspending agent, which is present in an amount of about 5% wt of suspending agent/wt of fertilizer concentrate
and water in an amount of about 30% wt of water/wt of fertilizer concentrate to about 40% wt of water/wt of fertilizer concentrate.

8. The fertilizer concentrate of claim 7, wherein said dithiocarbamate is a member selected from mancozeb, maneb, zineb, thiram and metiram.

9. The fertilizer concentrate of claim 7, wherein said phosphite salt is a member selected from monopotassium phosphite, dipotassium phosphite, calcium phosphite, monoammonium phosphite, diammonium phosphite, calcium hypophosphite and potassium hypophosphite.

10. The fertilizer concentrate of claim 9, wherein said phosphite salt is calcium phosphite.

11. A method of providing a fertilizer and a fungicide to a plant, said method comprising:
(a) mixing water and the fertilizer of claim 6, thus forming a use-dilution fertilizer; and
(b) applying said use-dilution fertilizer to the foliage of a plant, thus providing said fertilizer and said fungicide to a plant.

12. A fertilizer concentrate comprising:
a dithiocarbamate; and
at least one phosphite salt,
without the presence of dispersants or wetting agents, wherein said fertilizer concentrate is in a solid form.

* * * * *